(12) United States Patent
Felmlee et al.

(10) Patent No.: US 7,678,063 B2
(45) Date of Patent: Mar. 16, 2010

(54) MOTION MONITOR SYSTEM FOR USE WITH IMAGING SYSTEMS

(75) Inventors: Joel P. Felmlee, Rochester, MN (US); Russell E. Bruhnke, Rochester, MN (US); Phillip Rossman, Rochester, MN (US); James P. Potter, Sr., Rochester, MN (US); Stephanie K. Carlson, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 431 days.

(21) Appl. No.: 11/638,162

(22) Filed: Dec. 13, 2006

(65) Prior Publication Data

US 2007/0172029 A1    Jul. 26, 2007

Related U.S. Application Data

(60) Provisional application No. 60/757,196, filed on Jan. 6, 2006.

(51) Int. Cl.
*A61B 5/08* (2006.01)
(52) U.S. Cl. .................. 600/534; 600/529; 600/538
(58) Field of Classification Search ......... 600/529–543; 378/95, 94
See application file for complete search history.

(56) References Cited

U.S. PATENT DOCUMENTS

| | | | | |
|---|---|---|---|---|
| 2,196,909 A | * | 4/1940 | Bradford | 600/484 |
| 2,538,125 A | * | 1/1951 | Reid | 600/484 |
| 3,340,867 A | * | 9/1967 | Kubicek et al. | 600/526 |
| 3,524,058 A | * | 8/1970 | Wagoner, Jr. et al. | 378/95 |
| 4,258,718 A | * | 3/1981 | Goldman | 600/409 |
| 4,308,872 A | * | 1/1982 | Watson et al. | 600/538 |
| 4,807,640 A | * | 2/1989 | Watson et al. | 600/534 |
| 4,815,473 A | * | 3/1989 | Watson et al. | 600/534 |
| 4,889,131 A | * | 12/1989 | Salem et al. | 600/484 |
| 5,046,427 A | * | 9/1991 | Rowzee et al. | 102/418 |
| 5,178,151 A | * | 1/1993 | Sackner | 600/485 |
| 5,242,455 A | | 9/1993 | Skeens et al. | |
| 5,277,194 A | * | 1/1994 | Hosterman et al. | 600/534 |
| 5,301,678 A | * | 4/1994 | Watson et al. | 600/534 |
| 5,363,844 A | | 11/1994 | Riederer et al. | |
| 5,482,042 A | * | 1/1996 | Fujita | 600/428 |
| 5,543,012 A | * | 8/1996 | Watson et al. | 156/440 |
| 5,611,349 A | * | 3/1997 | Halleck et al. | 600/534 |
| 5,622,164 A | * | 4/1997 | Kilis et al. | 128/200.24 |

(Continued)

OTHER PUBLICATIONS

Carlson et al., Intermittent-Mode CT Fluroscopy-guided Biopsy of the Lung or Upper Abdomen with Breath-hold Monitoring and Feedback: System Development and Feasibility, Radiology 2003, 229:906-912.*

(Continued)

*Primary Examiner*—Charles A Marmor, II
*Assistant Examiner*—Jordan Golomb
(74) *Attorney, Agent, or Firm*—Quarles & Brady LLP

(57) ABSTRACT

A bellows-based patient breath-hold monitoring and feedback system for use in intermittent mode CT fluoroscopy-guided biopsies of the lung or upper abdomen where respiratory motion is a problem. Breath-hold monitoring and feedback with the bellows system allows a patient to perform consistent breath-holds at a preselected level, which in turn, optimizes intermittent mode CT fluoroscopy-guided biopsies of the lung or upper abdomen by allowing target lesions to be reliably visualized.

14 Claims, 6 Drawing Sheets

U.S. PATENT DOCUMENTS

| | | | | | |
|---|---|---|---|---|---|
| 5,727,562 | A | * | 3/1998 | Beck | 600/534 |
| 5,825,293 | A | * | 10/1998 | Ahmed et al. | 340/573.1 |
| 6,144,874 | A | * | 11/2000 | Du | 600/413 |
| 6,413,225 | B1 | * | 7/2002 | Sackner et al. | 600/529 |
| 6,561,987 | B2 | * | 5/2003 | Pail | 600/534 |
| 6,740,046 | B2 | * | 5/2004 | Knapp et al. | 600/538 |
| 7,050,537 | B2 | * | 5/2006 | Tsujii | 378/95 |
| 7,182,083 | B2 | * | 2/2007 | Yanof et al. | 128/204.23 |
| 7,367,955 | B2 | * | 5/2008 | Zhang et al. | 600/534 |
| 7,567,831 | B2 | * | 7/2009 | Miller et al. | 600/407 |
| 2003/0065272 | A1 | * | 4/2003 | Hillsman | 600/529 |
| 2003/0188757 | A1 | * | 10/2003 | Yanof et al. | 128/916 |
| 2003/0190010 | A1 | * | 10/2003 | Tsujii | 378/23 |
| 2004/0254492 | A1 | * | 12/2004 | Zhang et al. | 600/538 |
| 2005/0113673 | A1 | * | 5/2005 | Avinash et al. | 600/413 |
| 2006/0074300 | A1 | * | 4/2006 | Green | 600/427 |
| 2009/0175416 | A1 | * | 7/2009 | Yamanaka | 378/95 |

OTHER PUBLICATIONS

P.J. Robinson et al; Improved Control Of Respiration During Computed Tomography by Feedback Monitoring; Journal of Computer Assisted Tomogrpahy 6(4):802-806 August, New York.

H. Frohlich et al; Technical Developments and Instrumentation; RSNA, 1985.

K.R. Jones; A Respiration Monitor For Use With CT Body Scanning And Other Imaging Techniques; 1982, British Journal of Radiology 55, 530-533.

R.L. Ehman; Magnetic Resonance Imaging With Respiratory Gating: Techniques and Advantages; AJR 143:1175-1182, Dec. 1984.

G. Magreas; Initial Clinical Evaluation Of A Respiratory Gating Radiotherapy System; Proceedings of the 22nd Annual EMBS International Conference, Jul. 23-28, 2000.

S. K. Carlson, et al; Intermittent-Mode CT Fluoroscopy-Guided Biopsy of the Lung or Upper Abdomen With Breath-Hold Monitoring and Feedback: System Development and Feasibility; Radiology, Dec. 2003, vol. 229, No. 3, 906-912.

N. Tomiyama et al; CT-Guided Needle Biopsy of Small Pulmonary Nodules: Value of Respiratory Gating; Radiology 2000, 217:907-910.

Anzai Medical Co., Ltd; http://anzai-med.co.jp/eigo/az733v.htm; Respiratory Gating System.

B. Kavanagh; Active Breathing Coordinator Freeze Targets In Extracranial Stereotactic Radioablation, published brochure, 2 pages.

P.J.Robinson and K.R.Jones, Improved Control Of Respiration During Computed Tomography by Feedback Monitoring, Jour. of Computer Assisted Tomography, 6(4):802-806, Aug. 1982 Raven Press, New York.

H.Frohlick and W.Dohring, Technical Developments and Instrumentation, RSNA, 1985; 156-235.

R.L.Ehman et al, Magnetic Resonance Imaging with Respiratory Gating: Techniques and Advantages, AJR 143:1175-1182, Dec. 1984.

K.R.Jones, Technical Notes A Respiration Monitor For Use With CT Body Scanning and Other Imaging Techniques, 1982, British Journal of Radiology, 55, 530-533.

G. Mageras, et al, Initial Clinical Evaluation of a Respiratory Gating Radiotherapy System, Proc. of 22nd Annual EMBS International Conference, Jul. 23-28, 2000.

S.K. Carlson et al, Intermittent Mode CT Fluoroscopy-Guided Biopsy of the Lung of Upper Abdomen with Breath-Hold Monitoring and Feedback: System Development and Feasibility, Radiology, Dec. 2003, 906-912, vol. 229, No. 3.

Anzai Medical Co., LTD, Respiratory Gating System http://anzai-med.co.jp/eigo/az733v.htm, Sep. 5, 2003.

N.Tomiyama et al, CT-Guided Needle Biopsy Of Small Pulmonary Nodules: Value of Respiratory Gating; Radiology 2000; 217:907-910.

* cited by examiner

MOTION MONITOR SYSTEM FOR USE WITH IMAGING SYSTEMS

CROSS-REFERENCE TO RELATED APPLICATIONS

This application is based on U.S. Provisional Patent Application Ser. No. 60/757,196 filed on Jan. 6, 2006 and entitled "MOTION MONITOR SYSTEM FOR USE WITH IMAGING SYSTEMS".

BACKGROUND OF THE INVENTION

This invention relates generally to the field of medical apparati and more particularly to an apparatus to provide feedback regarding the movement of the body, for example, the lungs and the internal organs while breathing during imaging procedures, such as computer tomographic fluoroscopy.

Computer-aided tomography (CT) fluoroscopy is a technique used in medical diagnostics wherein x-rays impinge onto and are rotated around a patient to give a detailed real-time three-dimensional image of the interior of the body. CT fluoroscopy is especially useful during medical procedures because its rapid data acquisition and interpretation allow a physician to obtain a tissue sample or administer treatment while viewing the image.

CT fluoroscopy operates in two modes: continuous real-time mode and intermittent "quick-check" mode; and of the two continuous CT fluoroscopy results in a greater radiation exposure to both the patient and others in the vicinity of the patient. Quick accurate needle advancement or placement of treatment or biopsy apparatus into the body, moreover, is difficult with continuous CT fluoroscopy, even with a needle-holder or other device that may prevent or at least minimize exposure to the primary beam. Intermittent CT fluoroscopy, on the other hand, substantially decreases both patient and operator exposure to radiation, as a result, this technique is frequently used for incremental needle advancement and rapid verification of needle position during biopsies and/or administration of treatment.

The lungs, the diaphragm, and the upper abdomen move during breathing; thus the displacement of the body and its organs during the breath cycle can be a significant problem during certain medical procedures because target structures, such as lesions and tumors also move during breathing. Intermittent mode CT fluoroscopy allows imaging only in the axial plane with a slice thickness of three to seven millimeters. Inconsistent breath holding by a patient, especially during procedures performed in the area of the thoracic cavity, can cause target structures such as lesions or tumors to move completely out of sight during imaging and intervention. As an example, during normal breathing, tumors in the lung can move from one to three centimeters, and a diaphragm motion can cause the upper abdominal organs to move from one and a half to six centimeters in the superior-inferior direction. Despite instructions to reproducibly and consistently hold her/his breath, there is also a large variation in lung inflation and upper abdominal organ position even in patients with no known lung pathology. Once reproducibility is decreased, the procedures are prolonged and both the patient and medical personnel are exposed to more radiation. There is also the potential for decreased diagnostic yield of the biopsy specimen and higher complication rates.

Thus, accurate and safe CT fluoroscopy-guided percutaneous biopsies of the lung or upper abdomen require a patient to precisely and reproducibly hold or suspend her/his breath. Even healthy patients are unable to reproduce consistent levels of suspended inspiration or expiration without the help of breath-hold monitoring and feedback systems. These breath-hold monitoring systems coordinate the display or view of the area of interest with a feedback system that allows a patient to hold her/his breath at a particular position. Breath-holding monitoring and database systems have been used successfully in radiation therapy for delivery of radiation to selected moving targets thereby decreasing image artifacts secondary to respiratory motion. With breath-hold systems, the position of the diaphragm and internal organs varied less during suspended respirations than without the breath-holding feedback; e.g., average diaphragm motion decreased from 8.3 millimeters to 1.3 millimeters during magnetic resonance, and average diaphragm variability was reduced from 1.4 centimeters to 0.3 centimeters during radiation treatment. The drawback to the systems, however, is that they monitor external changes in body wall girth or position, rather than the actual physical display of the interior portions of the body; although these external changes may be correlated to diaphragm position and internal lesion location, as disclosed in Frolich et al., "A Simple Device For Breath-Level Monitoring During CT" 156 Radiology 235 (1985). Some of these systems, however, use a liquid mercury column respiration monitor, see Jones et al., "A Respiration Monitor For Use With CT Body Scanning And Other Imaging Techniques" 55 British Journal of Radiology 530 (1982). Most of these systems, moreover, linearly correlate the movement of the body to changes in pressure in the transducer, a presumption that is not always accurate. Still other breath holding and monitoring systems are disclosed in U.S. Pat. Nos. 5,363,844 and 5,242,455 and published U.S. patent application Ser. No. 2003/0188757 entitled "CT Integrated Respiratory Monitor".

There is thus a need for a sensitive, reliable and convenient monitoring system to detect motion and correlate that motion to real-time imaging procedures, such as correlation of the respiratory cycle in CT fluoroscopy-guided procedures, and provide feedback to a patient or other person. The system, moreover, preferably provides for patient and radiologist interaction and is adaptable for use in intermittent mode CT fluoroscopy-guided biopsies of the lung and upper abdomen.

SUMMARY OF THE INVENTION

The present invention is a motion detection system for use on a patient undergoing a medical procedure where it is important for the subject to repeatedly re-establish a reference position. The motion detection system includes a motion detector for sensing the motion of the subject and producing a motion input signal, a control unit for receiving this signal and producing displacement data indicative of subject motion away from a reference position, and one or more displays for receiving the displacement data and indicating the displacement of the subject from the reference position.

One aspect of the invention is the use of wireless communications between the control unit and the display units to enable the display units to be easily positioned within eyesight of the subject to provide real-time position feedback and within eyesight of others performing the medical procedure. This provides flexibility in the positioning of displays to account for variations in patient size and positioning and variations in the arrangement and complexity of equipment in the imaging suite.

Another aspect of the invention is a manually operable reference switch which enables an operator to establish a desired reference position anywhere within the respiratory cycle from which subject motion is measured. This also establishes the location of the dynamic operating range of the motion detector such that accurate displacement data is produced in the vicinity of the reference position even if the subject motion is greater than the dynamic operating range of the motion detector. This establishes a high resolution signal at the point of importance within the respiratory cycle.

DETAILED DESCRIPTION OF THE PREFERRED EMBODIMENT

Figure 1:
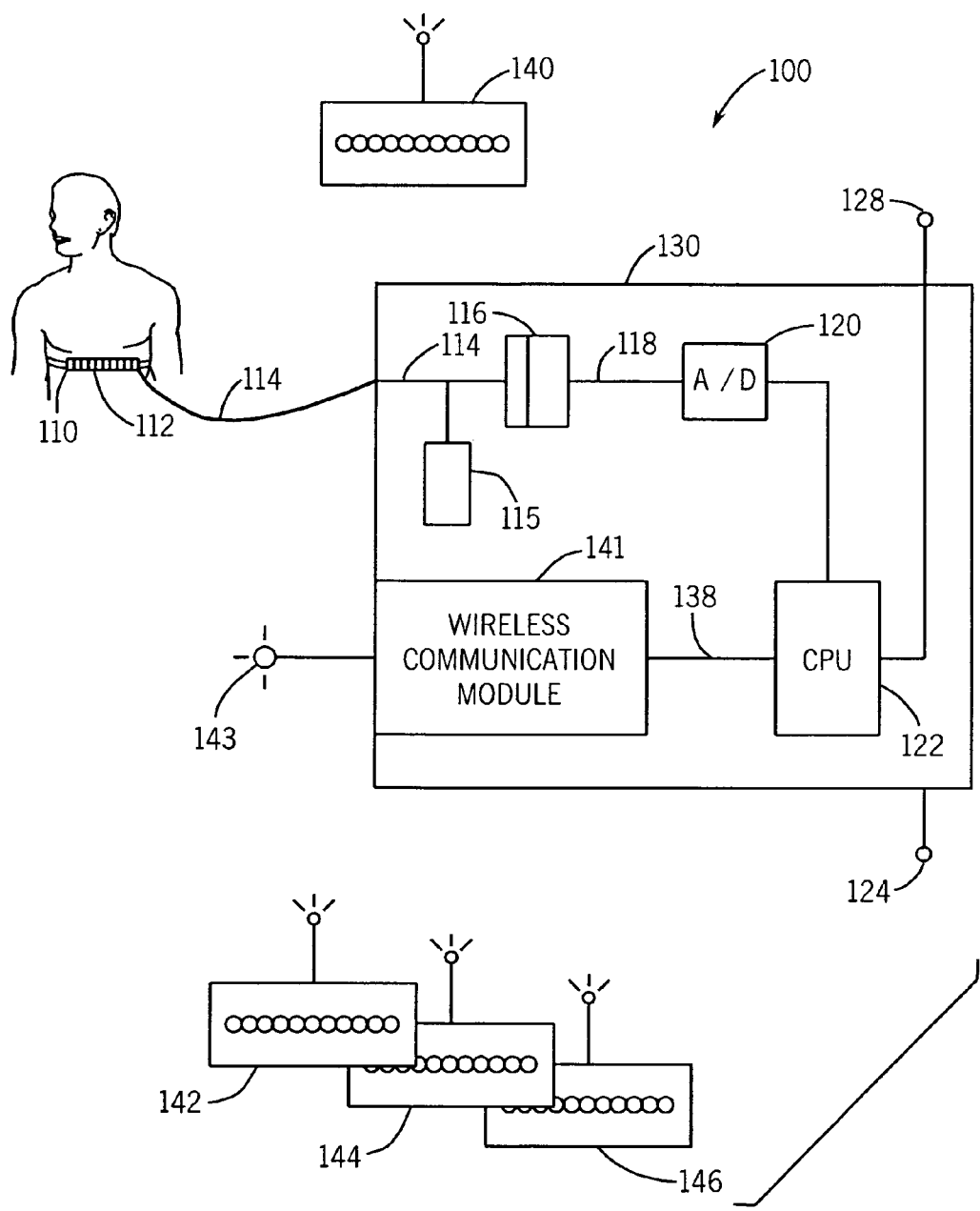
FIG. 1 is a simplified block diagram of the components comprising the bellows movement system in accordance with an embodiment of the invention.
Figure 2:
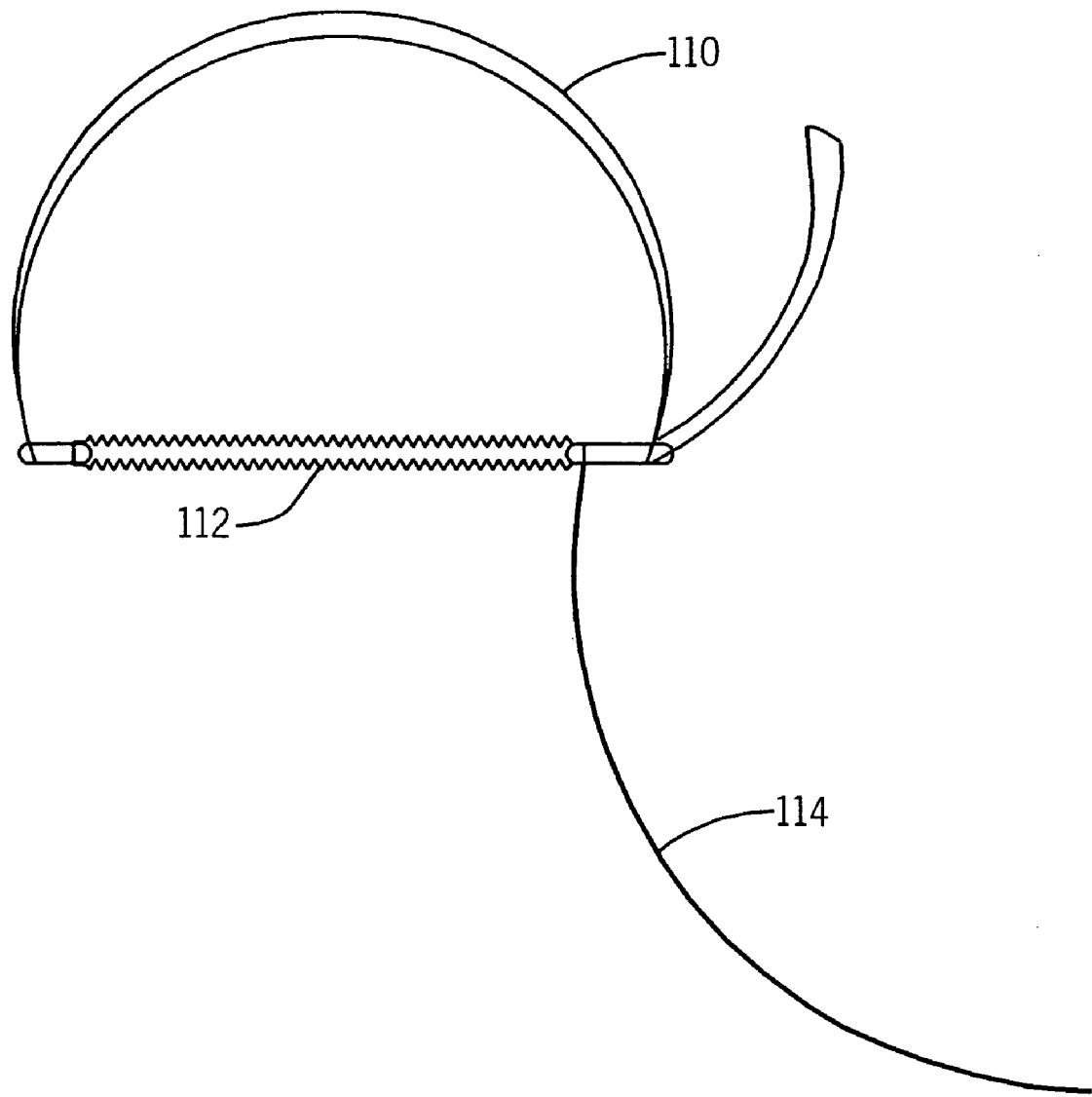
FIG. 2 is a pictorial view of the bellows, the belt, and the pressure tube of the bellows movement system of FIG. 1.

Referring to FIGS. 1 and 2, a motion detection and monitor system 100 includes an expandable bellows 112 connected on both ends to a strap or a belt 110. The bellows is a motion detector 112 constructed from flexible rubber, silicone, or other expandable material responsive to expanding and contracting chest motion. The strap 110 may be cloth or leather having Velcro or D-rings or other attachment mechanism to circumscribe the body. A hollow tubing 114 containing a gas, preferably ambient air is connected to the interior of the bellows. Changes in patient girth occurs during respiration and this result in expansion and contraction of the tubing 114. Other motion detectors 112 may also be used such as a strain gauge or piezoelectric fabric.

The belt 110 is positioned around a patient's upper abdomen or lower chest. When the motion to be detected is the respiratory motion, it is preferable to position the motion detector or bellows 112 on the anterior of the body at a location having the greatest displacement during breathing, particularly during inspiration. Positioning of the patient will impact the anatomic location that produces maximum motion during breathing, but patients are often abdominal breathers and the ideal placement of the motion detector 112 in these patients is usually just below the xiphoid. The detector's sensitivity to motion preferably is unaffected by whether the patient is in the supine (lying on the back with the face upward), lateral decubitus (lying on one's side), or prone (lying face down) positions, although there tends to be less respiratory excursion in the prone position than in the supine and decubitus positions.

As the body moves the detector 112 expands and changes shape and generates a signal. When the bellows motion detector 112 expands the air pressure in the attached tubing 114 decreases. When the bellows motion detector 112 contracts, the air pressure in the attached tubing 114 increases The tubing 114 is connected to a control unit 130 that includes a pressure sensitive transducer 116 that detects the change of pressure of the gas within the tubing 114. The transducer 116 may be located either within or without the control unit 130, but is preferably within the control unit 130 with the other electronics. In an alternative embodiment wherein the motion detector is a piezoelectric fabric or a strain gauge, an electric signal will be generated in response to the motion of the body and input directly to the control unit 130, or generate appropriate signals to a remote display.

A solenoid valve 115 is mounted in the control 130 and controls the pressure within tubing 114 and detector 112. Solenoid valve 115 has two ports. One port connects to tubing 114 and the other port remains open to atmospheric air. In the open position of solenoid valve 115, the two ports are connected and the pressure within tubing 114 and detector 112 remains at atmospheric level even as the detector expands or contracts. Once solenoid valve 115 is closed, the two ports are isolated and the pressure of the gas in tubing 114 varies as detector 112 expands and contracts. Solenoid valve 115 is controlled by CPU 122 as will be described below.

Transducer 116 is a two port device that compares the pressure between the two ports and generates a proportional analog signal 118. One port connects to tubing 114 and the other port is left open to ambient pressure. The transducer 116 generates an analog input signal 118 in response to the change of pressure in tubing 114 with respect to ambient pressure. A positive voltage is generated if the pressure in tubing 114 is higher than ambient and a negative voltage is generated if the pressure in tubing 114 is less than ambient. Because the motion detector input signal 118 is dependent on the pressure differential between two ports, and the fact that one port is open to ambient pressure, the system can be used in any ambient pressure.

The motion detector input signal 118 is digitized by an analog-to-digital converter 120, and the digitized signal 118 is input to a central processing unit 122 which is a commercially available microcomputer. The CPU 122 processes the input signal 118 and produces a feedback signal at output 138. Using a calibration mode described in detail below, the input signal 118 voltage level is scaled by a factor that matches one diode of display to 1.3 mm of physical displacement (either compression or elongation) of the bellows. This calibration factor represents the change in patient girth that has been shown to correlate with 3.5 mm superior-inferior motion of the patient's diaphragm. The signal polarity is determined as positive or negative relative to the reference location. The amplitude of the input signal 118 is processed by CPU 112 to produce an integer number of calibrated 1.3 mm steps as determined by a stored diode curve describe below. The number of steps indicated by feedback signal 138 determines the patient feedback signal on a display described below. For example, if the input signal is minus 3.5 volts, with a measured system calibration factor of 1.5 volts/diode the feedback signal 138 would reflect 3.5 volts divided by 1.5 volts per display diode. As a result, one display light emitting diode is turned on and located two diodes below (due to the negative signal polarity) the center light emitting diode (which acts as the reference). If the input signal were plus 3.5 volts in the above example, the feedback signal would be one diode turned on and located two diodes above the reference center diode. This feedback signal 138 is coupled to one or more displays 140, 142, 144, 146 by a wireless communications module 141. The CPU 122 may also produce other output signals at 124 which are coupled to work stations or the imaging system being used to perform the scan.

Figure 6:
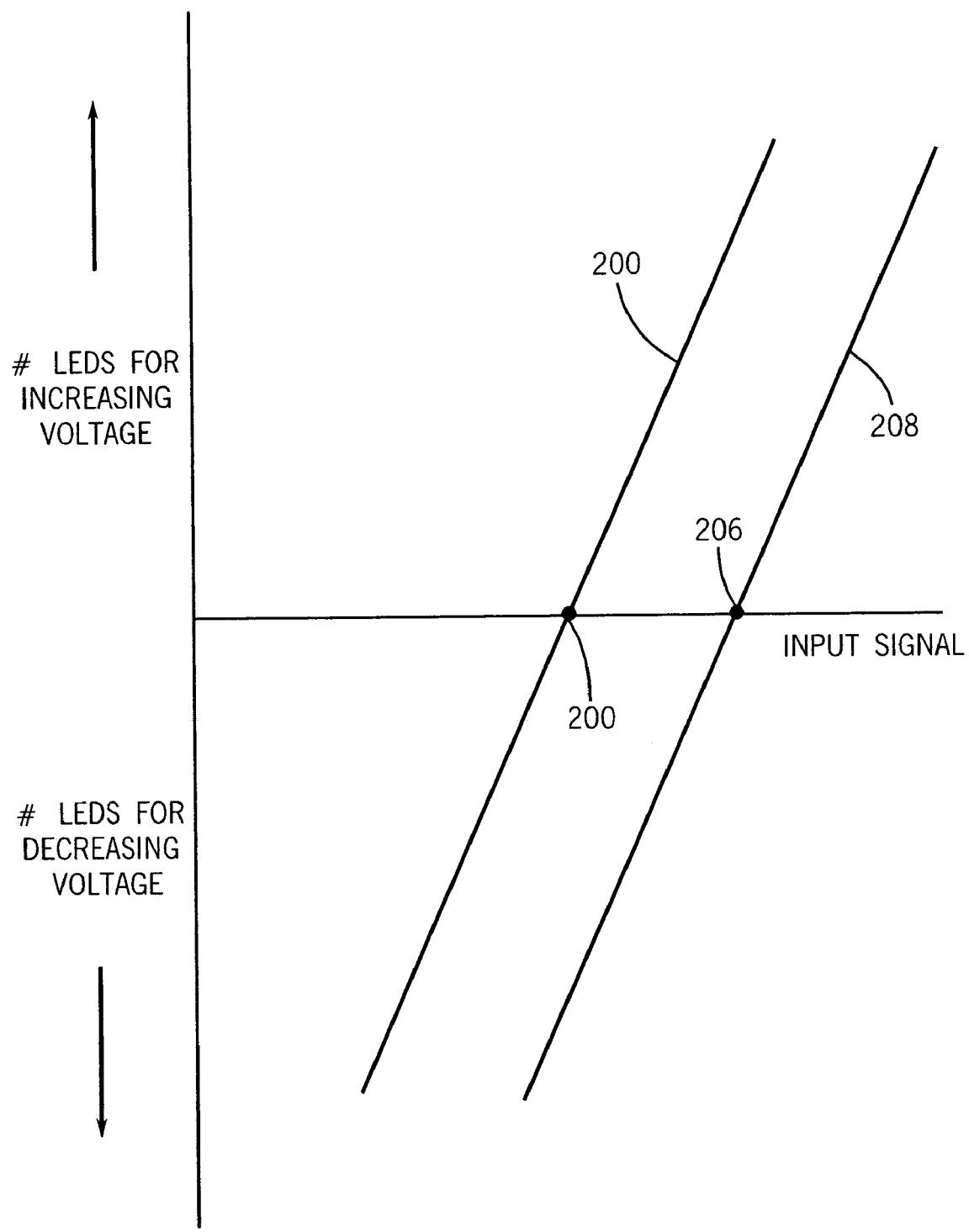
FIG. 6 is a graphic representation of diode curve stored in the control unit of FIG. 3.

During power-up the CPU 122 enters the calibration mode and performs a number of function related to a diode curve stored in CPU 122. This diode curve determines the bellows motion that is required to turn on or off a light emitting diode on the display. The preferred embodiment uses a linear curve shown in FIG. 6, but a non-linear curve may be more appropriate in certain circumstances. The diode curve is symmetrical about a center point. This center point correlates a center LED 350 on the display described below with the analog input signal 118 generated by transducer 116 when both ports are at ambient pressure. The center point of the curve is adjustable by CPU 122. When power is first applied, CPU 122 opens solenoid valve 115 to connect tubing 114 and bellows motion detector 112 to ambient pressure. This action ensures that both ports of transducer 16 are also at the same ambient pressure. The signal generated by the transducer is digitized by the A/D 120 and read by CPU 122. CPU 122 compares this signal with the default center point of the stored diode curve. CPU 122 shifts the curve to account for any input signal difference. Referring to FIG. 6, curve 200 is the default diode curve stored in the CPU 122 with a center point 204. When the system runs the calibration routine at power-up, a new center point 206 is determined. CPU 122 then shifts the entire diode curve to the new center point 206 resulting in a calibrated diode curve 208.

The wireless communications module 141 uses modules designed to transmit within the ISM band frequency range. It transmits signals at an antenna 143 which are received at antennas on the respective displays 140, 142, 144 and 146. The display 140 is positioned within easy eyesight of the patient being scanned, and the other displays are positioned where needed. For example, one display 142 may be positioned within easy eyesight of the physician performing the procedure and another display 144 may be positioned near the imaging system operator console. Since the displays are wireless battery operated devices, they can easily be placed where needed and adjusted for the best possible viewing angle.

Wireless communication modules 141 can also use a transceiver which enables data to be sent to the displays and also received from them. This bi-directional communication can be used for data integrity protocols and to allow various functions to be placed at the display, such as a remote reference switch.

Any number of wireless displays 140-146 can be used with the system. A system consists of one control unit 130 and at least one display. Each display has a unique serial number. To establish which displays a particular control unit 130 can communicate with, each display 140-146 is temporarily connected to control unit 130 at a port 128. The CPU 122 then performs an identification procedure in which it communicates with the display and retrieves a display serial number stored therein and saves therein a unique group code. The group code is unique for each control unit 130. This action is called synchronization. During wireless communication, control unit 130 sends the group code imbedded in the data. Only displays that have been synchronized to this group code will respond. In the same fashion, the displays can send data to control unit 130. Their serial number is imbedded in the data stream and control unit 130 will only respond to displays that have been synchronized. This technique allows any display to become part of the system and allows multiple systems to be operated simultaneously in adjacent exam rooms without interfering with each other. The control unit group code and the display unit serial number are unique and are programmed at manufacturing.

One skilled in the art will appreciate that while respiratory motion is detected above, the motion detection system 100 can be used to monitor other motions of the body. The invention can be used with or without imaging, and it may be used to monitor the capacity of the body to move. For example, the output of the motion detection and monitor system 100 can be correlated to lung capacity, or the angle of rotation of a shoulder, or other motion. These motions can be advantageously mathematically modeled by the CPU 122, or the signal can be conditioned in the CPU 122 for export to other processing systems. In the prior art systems, the movement of the body was presumed to be linear; but by incorporating a CPU 122 into the system 100, different mathematical models of motion can be programmed into the CPU to accommodate three-dimensional and other parametric motion models along with nonlinear calibration models used to correct for input signal or system nonlinearity.

Figure 3:
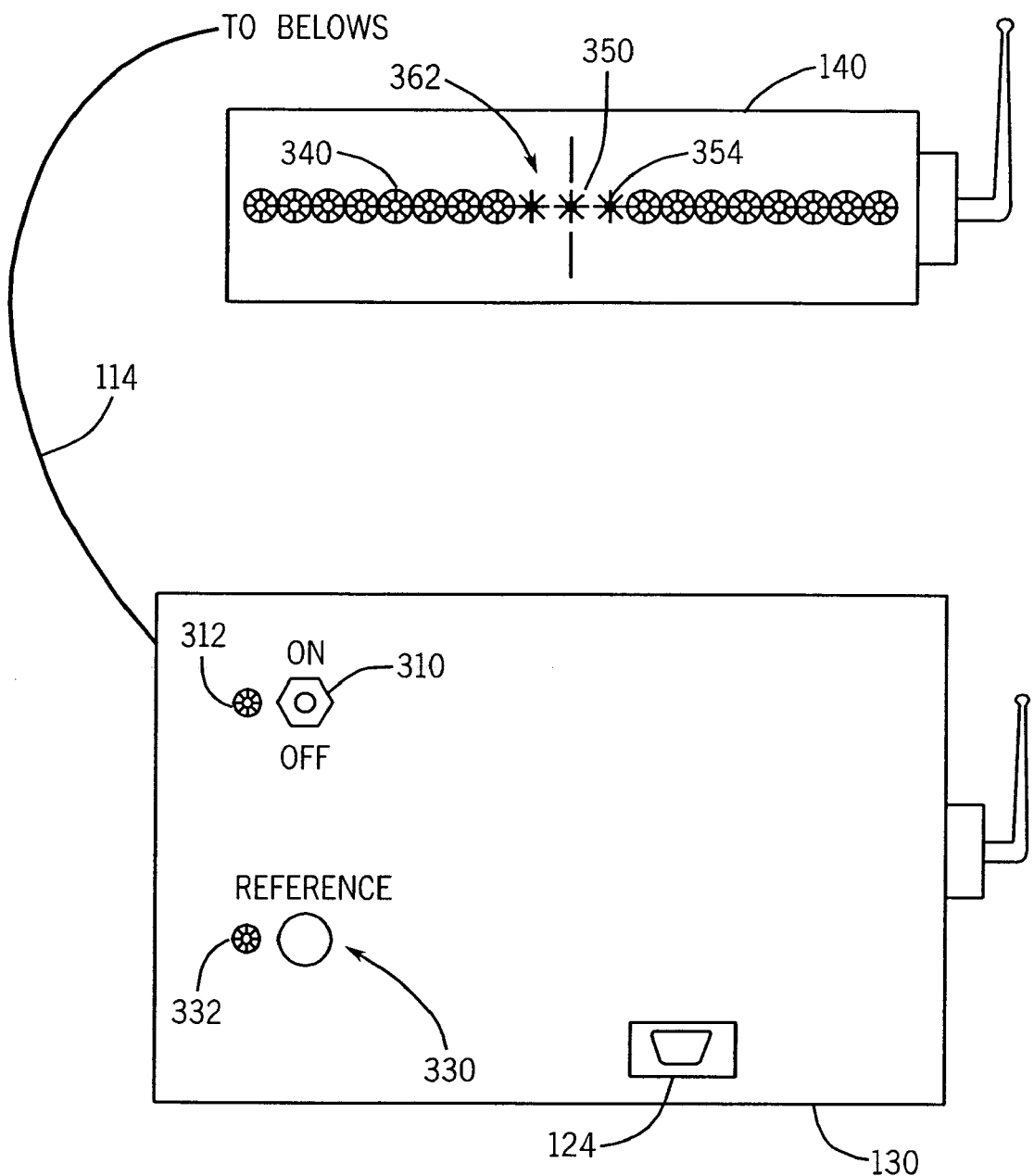
FIG. 3 is a pictorial view of the control unit and a display which form part of the system of FIG. 1.

Referring particularly to FIG. 3, the control unit 130, includes a front panel which supports two switches: a power switch 310 and a reference switch 330. The power switch 310 provides an operating voltage to the electronics within the control unit 130 and a light 312 indicates that power is provided to the control unit 130. The reference switch 330 allows the air pressure within the bellows system to equilibrate with the ambient air pressure to determine the correct reference point during the power-on phase. The reference switch 330 is an input to CPU 122, and when it is pressed, CPU 122 opens or closes solenoid valve 115. As described above, when the solenoid 115 is closed a positive or negative pressure can occur in the tubing 114 in response to patient motion and this is converted to the input signal 118 by transducer 116. A light 332 is energized when the solenoid valve 115 is operated.

Referring still to FIG. 3, the display 140 that is located within eyesight of the patient has a row of light emitting diodes 340, the center three of which 362, 350, 354 are colored differently than the others for ease of viewing. The control unit 130 communicates wirelessly with the patient display 140 and with the additional displays 142-146. As described above, a reference position is established and as a patient inhales from this reference position, the diodes 340 will sequentially light from the center 350 to either the right or left. The further the patient's girth changes from the reference position, the larger the number of diodes 340 that are lit. When the patient exhales, the number of lit diodes 340 will at first decrease until the reference (center diode 350) is lit and then the light emitting diodes 340 sequentially light in the opposite direction. Thus, with calibration, the lit diodes 340 on the display 140 actually represent a distance, or displacement of the detected patient motion in either direction from a reference position. The motion detection system is calibrated so that a lit diode 340 represents a unit of displacement. Thus, the patient is able to use an objective/quantitative display 140 as a feedback device that enables the patient to reliably and repeatedly during an examination reproduce a position or a respiratory level that may be critical in their treatment.

Figure 4:
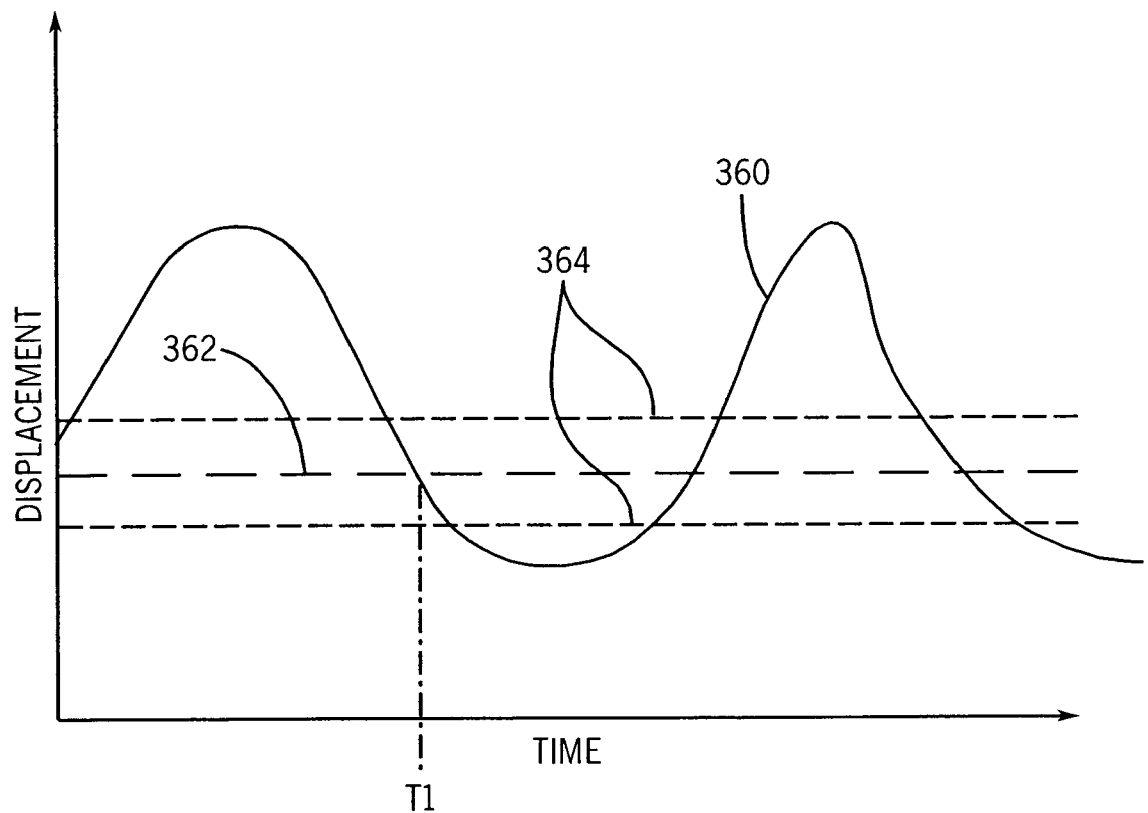
FIG. 4 is a graph of respiration motion monitored by the system of FIG. 1.

A further advantage of the reference function is that the transducer 116 may be selected to have a high sensitivity. Referring particularly to FIG. 4, a normal respiratory cycle is shown at 360 and is typically sinusoidal in nature. The sensitivity of the transducer 116 is selected such that a change in bellows position, or displacement needed to increase or decrease by one the number of lights 340 that are lit on display 140 is 13 mm. However, the dynamic range of motion during the respiratory cycle is well beyond 100 mm which means the transducer output signal will saturate outside a very small range of respiratory displacement values. Proper operation in this large dynamic range is achieved by directing the patient to breath hold at a desired point in the respiratory cycle and then press the reference switch 330 to establish a reference point. As explained above, this opens solenoid valve 115 briefly allowing a new reference zero pressure and input voltage level to be established at the desired respiratory phase, or level. For example at time ti the reference switch 330 may be operated to establish a reference point indicated by dashed line 362. The dynamic range of the display 140 at a sensitivity of 13 mm per light 340 will span only a part of the respiratory cycle 360 as indicated by dotted lines 364. However, it spans that portion of the respiratory cycle deemed important by the physician at a high resolution. The display 140 will be out of range during large parts of the respiratory cycle, but when the patient approaches the desired breath hold point, the lights 340 on the display 140 begin changing to provide the patient and attending physician with feedback as to respiratory phase. The patient adjusts the breath hold until only the center light 350 is lit, and when this is achieved, the displacement is back to the reference location with an accuracy of ±6.5 mm change in abdominal girth, and ±1.75 mm change in S/I diaphragm position.

Figure 5:
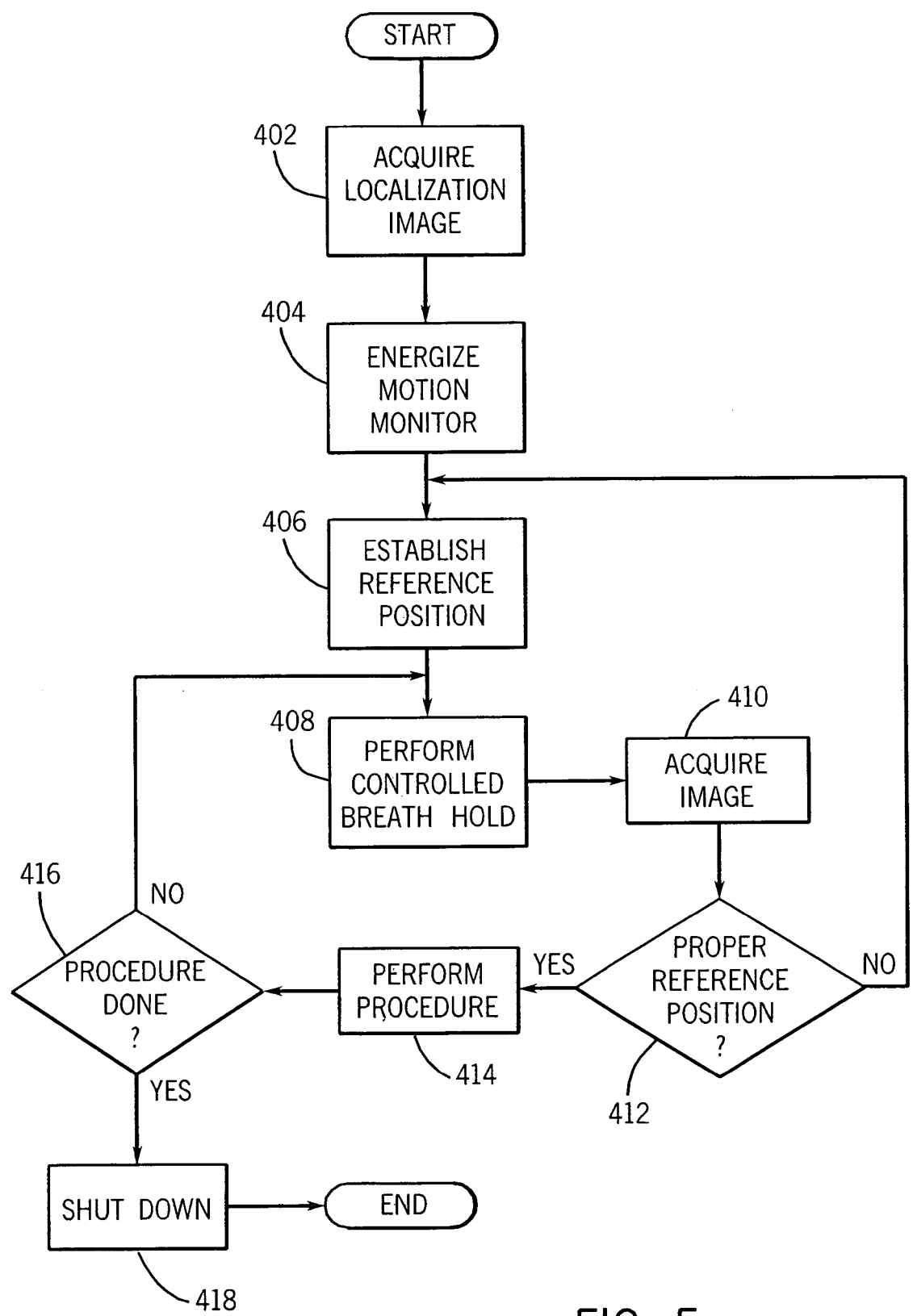
FIG. 5 is a flow chart of the process by which the bellows movement system of FIG. 1 monitors patient respiration.

Referring particularly to FIG. 5, the motion monitor system may be used during an image guided procedure such as a biopsy. As indicated at process block 402, the first step is to position the patient in the medical imaging system and acquire a localization image. This is used to properly position the patient and adjust the scan prescription such that the target of the procedure, such as a tumor, is optimally seen.

As indicated at process block 404, the motion monitor 130 is then energized and the patient is told to breathe normally. The patient is then instructed to breath-hold and a reference position is established at this point as indicated at process block 406. This is performed by momentarily depressing the reference switch 330 on the motion monitor 130 (see FIG. 3).

A loop is then entered in which the patient performs a series of controlled breath-holds, images are acquired to guide the physician and the medical procedure is performed. As indicated at process block 408, the patient is instructed to control breathing until only the center light 350 on display 140 is lit and then hold their breath. Seeing that a successful controlled breath-hold is being achieved, the physician then initiates an image acquisition as indicated at process block 410. The acquired image is displayed immediately and the physician can judge whether or not the proper breath-hold reference point has been established. If not, as indicated at decision block 412, the procedure loops back to establish another reference position at process block 406. For example, the physician might instruct the patient to breath until a specific number of lights to the right or left of the center light 350 on display 140 are lit and then the reference switch 330 is again depressed to establish this point as the new reference. This may be repeated a number of times until the target lesion is moved to a location that is optimally accessible to a biopsy needle or the like as seen in the acquired image.

Referring still to FIG. 5, when the optimal breathhold reference position is established the procedure may be performed by the physician as indicated at process block 414. During the procedure the physician may acquire additional images at 410 to help guide an instrument into position and to help perform an operation with that instrument. At all times the physician observes a motion monitor display which is conveniently positioned for the physician to see. The physician is thus insured that the patient is maintaining a breath hold at the proper reference position. Of course, the patient will periodically breath and then re-establish the proper reference position breath hold as indicated at process block 408. When the procedure is completed as indicated at decision block 416, both the imaging system and the motion monitor are shut down as indicated at process block 418.

A bellows-based motion detect system has been calibrated to determine the approximate change in position of the diaphragm during breathing per one unit change in diode position on the patient's visual display, i.e., how many millimeters of diaphragmatic motion does one diode represent? Using the bellows system while undergoing sagittal single-shot fast spin echo (SSFPE) magnetic resonance imaging, the breath cycle of human volunteers was monitored. Each person held her/his breath while attempting to return the feedback signal to only the center diode of the visual display during twenty consecutive breath-holds, ten on inhalation and ten on exhalation. To determine the number of millimeters displacement per diode, the volunteers held their breath at different levels, e.g., they held their breath at a position so that only the center diode was lit, then they held their breath so that only the diode above/below the center diode was lit; then they held their breath so that the next diode above/below the center diode was bright, and so on. During each breath-hold attempt, using a magnetic resonance imager display program, the internal position of the diaphragm and a specified blood vessel in the lower lung in relation to a previously placed external chest wall marker was measured and recorded. Mean diaphragm and blood vessel positions along the z-axis, i.e., from the front of the body to the back of the body, and standard deviations were calculated. Linear regression techniques determined the correlation of diaphragm and blood vessel position with change in body girth as measured by the bellows system. The bellows system consistently detects body wall motion at nominal levels of one-millimeter deflection, well below the minimal criteria for clinical usefulness of five millimeters. The mean coefficient of variation over a range of respiratory amplitudes was 1.12, with a range of 0.69 millimeters to 9.94 millimeters, with a standard deviation of 0.55 millimeters.

There is a linear correlation between breath-hold level, i.e., lit diode position, and z-axis motion representing internal target diaphragm and vessel locations with an $r^2$ of 0.84 to 0.94. Calculation of the slope of the linear regression line helped to determine the number of millimeters per one unit change in diode position. Measurements of diaphragm and lower lung blood vessel position show an average change of 3.5 millimeters per diode and 2.5 millimeters per diode, respectively. During small inspiration, the standard deviation about the mean breath-hold level for diaphragm position ranged from 0.73 millimeter to 2.7 millimeters with a mean of 1.7 millimeters; the displacement of a lower lung blood vessel position ranged from 0.58 millimeter to 1.9 millimeters with a mean of 1.1 millimeters. During expiration, the value of diaphragm position varied from 1.1 millimeters to 2.0 millimeters with a mean of 1.5 millimeters, and for lower lunch blood vessel displacement from 0.5 millimeters to 2.8 millimeters with a mean of 1.6 millimeters.

In patients with small lesions of less than one centimeter, it is preferred that a patient hold her/his breath when the center diode is lit. In patients with larger lesions, the lesion may still be adequately visualized even if the patient has difficulty returning the feedback signal to the center diode but is able to consistently return to within one diode above or below the center reference.

Additional displays adapt the bellows system to an actual CT fluoroscopy environment. One display is, of course, visible to the patient. Another display may be attached to a CT fluoroscopy monitor so that the radiologist can visualize when the patient is at the appropriate breath-hold level, a third display may be attached to the system control unit next to the CT operation console so that patient breath-hold levels can be monitored and correlated with localization CT scans. Use of multiple displays allows a team of people caring for the patient to know when the exact motion position or respiratory level is achieved, so that the other care which may be dependent upon the position or respiratory level, can begin or continue. The bellows system may be installed on an interventional CT scanner, such has a HiSpeed CT/I scanner with SmartView CT fluoroscopy; GE Medical Systems, Milwaukee, Wis.

The bellows system has been used to monitor breath of patients undergoing intermittent mode CT fluoroscopy-guided biopsy of mobile lesions of the lung, liver, kidney, and adrenal gland. The time required to install the bellows system and train the patient is slight, on the order of five minutes or so. It is important to note that all the patients were able to consistently reproduce the selected motion position or breath-hold level during consecutive movement or breath-hold attempts using the bellows system. It is also of consequence to note that the motion-hold position or breath-hold level was correlated to optimal visualization of the target lesion throughout the procedure. In all cases, the lesions were successfully punctured; only one puncture was required in nine cases, and in only one case were two punctures necessary to access the lesion. The size of the lesions ranged from 0.7 centimeter to 2.3 centimeters with a mean lesion size of 1.6 centimeters. The CT fluoroscopy exposure time ranged from 4.8 seconds to 34.8 seconds with a mean of 16.9 seconds; advancement of the needle, and successful puncture of the lesion, ranged from 3 minutes to 25.5 minutes with a mean of 11.5 minutes.

The motion detection system is particularly beneficial and useful during biopsies of small peripheral lung lesions because the ribs often overlie and conceal the small lesions, making them difficult to access. The motion detection system enables the patient to obtain different levels of motion, such as inspiration or expiration, until the radiologist finds the best position or breath level for optimal access to the lesion. Another circumstance where the motion detection system has been particularly useful is to minimize or eliminate changes in breath-hold level that occur between the pre-procedure localization images and the start of the procedure. Particularly, levels of inspiration or expiration can change dramatically because the patient may be experiencing pain or anxiety, or because a patient has been given intravenous conscious sedation or relaxation medication. The motion detection system decreases the variation resulting from these factors and allows the patient to reproduce the reference motion-hold or breath-hold level obtained during the localization images. The display distracts nervous or anxious patients by requiring them to concentrate on their motion or breath rather than on the actual procedure. In a sedated patient, the motion detection system, particularly the bellows-based system, can assist personnel in stimulating the patient to take in adequate air, thereby maintaining the patient's oxygen saturation in the normal range. The bellows system is also helpful in parenchymal biopsies of the upper abdomen when the lesion cannot be visualized following washout of the intravenous contrast material. If the patient reproduces the same motion-hold or breath-hold level as on the contrast-enhanced study when the lesion was visualized, the radiologist can use landmarks to access the lesion even though it is no longer seen on the CT fluoroscopy images.

While the description provides embodiments of the invention, the embodiments are considered illustrative and by way of example only and are not intended to be limiting. For example, one embodiment of the invention has been presented as monitoring the movement of the internal organs, the diaphragm, and the lungs during breathing to assist in computer aided tomographic procedures. The motion detection system may also be used during ultrasound examinations or in connection with other imaging systems. Also, whereas the displays use visible lights to provide the patient with respiratory feedback, for blind patients the displays can be changed to indicate with sound the respiratory feedback information.

The invention claimed is:

1. A motion detection system for monitoring a range of motion of a subject during a medical procedure, the combination comprising:
   a motion detector positioned to measure subject motion and produce an input signal;
   a control unit connected to receive the input signal from the motion detector and being operable in response thereto to produce displacement data indicative of subject motion from a reference position;
   a display having multiple indicators, each of which represents a unit of displacement from the reference position, wherein a total of the units of displacement defines an operational range of the display, and wherein the operational range of the display is less than the range of motion of the subject;
   a wireless communication link between the control unit and the display for conveying the displacement data from the control unit to the display such that the display indicators provide feedback to the subject; and
   a reference switch configured to allow manual selection of a portion of at least one of a dynamic range of the motion detector and the range of motion of the subject over which the operational range of the display operates.

2. The motion detection system of claim 1, wherein the motion detector includes:
   a deformable gas-filled bellows;
   a tubing filled with the same gas as the bellows, a first end of the tubing connected to an interior of the bellows;
   a reference valve connected to the tubing and being operable when operated to couple the interior of the tubing to the surrounding ambient air and to thereby equalize the pressure therein with the ambient air pressure; and
   a transducer connected to a second end of the tubing and being operable to produce the input signal in response to the pressure on the interior of the tubing.

3. The motion detection system as recited in claim 2 in which the control unit includes a switch for manually energizing the reference valve.

4. The motion detection system as recited in claim 1 which includes an additional display that receives displacement data from the control unit using the wireless communications link.

5. The motion detector system as recited in claim 1 in which the display includes a plurality of discrete displacement markers and the display is configured to operate according to a non-linear curve that determines an amount of subject motion from the reference position that causes a change in the displacement markers.

6. The motion detector as recited in claim 5 in which the discrete displacement markers include a plurality of a light emitting diodes.

7. A motion detection system for monitoring the respiratory motion of a subject during a medical procedure, the combination comprising:
   a motion detector for sensing the respiratory motion of the subject and producing an input signal, the sensitivity of the motion detector being set such that the dynamic range of the motion detector input signal is substantially less than the dynamic range of subject motion during a complete respiratory cycle;
   a control unit connected to receive the input signal from the motion detector and being operable in response thereto to produce displacement data indicative of subject motion from a reference position;
   a display coupled to the control unit for indicating the displacement of the subject from the reference position; and a reference switch which is coupled to the motion detector and is manually operable to establish a reference position in the subject's respiratory cycle from which displacement is measured.

8. The motion detection system as recited in claim 7 in which the motion detector includes a bellows which deforms in shape in response to respiratory motion of the subject to change air pressure therein, and a transducer which produces the input signal in response to the air pressure in the bellows.

9. The motion detector system as recited in claim 8 in which the reference switch operates a solenoid valve to equilibrate pressure in the bellows with surrounding ambient pressure.

10. The motion detector system as recited in claim 7 in which the control unit stores a curve that relates the input signal to subject motion and the operation of the reference switch shifts the operating range of the stored curve.

11. The motion detector system as recited in claim 10 in which the motion detector includes a bellows which deforms in shape in response to respiratory motion of the subject to change air pressure therein, and a transducer which produces the input signal in response to the air pressure in the bellows.

12. The motion detector system as recited in claim 11 in which the reference switch operates a solenoid valve to equilibrate pressure in the bellows with surrounding ambient pressure.

13. The motion detector system as recited in claim 7 in which the display includes a plurality of discrete displacement markers and the display is configured to operate according to a non-linear curve that determines an amount of subject motion from the reference position that causes a change in the displacement markers.

14. The motion detector as recited in claim 7 in which the discrete displacement markers include a plurality of a light emitting diodes.

* * * * *